United States Patent [19]

Zatsepin et al.

[11] 4,207,519

[45] Jun. 10, 1980

[54] METHOD AND APPARATUS FOR DETECTING DEFECTS IN WORKPIECES USING A CORE-TYPE MAGNET WITH MAGNETO-SENSITIVE DETECTORS

[75] Inventors: Nikolai N. Zatsepin; Alexandr P. Gusev, both of Minsk, U.S.S.R.

[73] Assignee: Otdel Fiziki Nerazrusha-Juschego Kontrolya Akademii Nauk Belorusskoi S.S.R., U.S.S.R.

[21] Appl. No.: 909,574

[22] Filed: May 25, 1978

[51] Int. Cl.² .................... G01R 33/00; H01L 43/00
[52] U.S. Cl. .................................. 324/235; 324/238
[58] Field of Search ............... 324/228, 234, 235, 238, 324/239-242

[56] References Cited

U.S. PATENT DOCUMENTS 3,359,495  12/1967  McMaster et al. ............... 324/235
3,846,697  11/1974  Cila et al. ............................. 324/228

OTHER PUBLICATIONS

Shiraiwa et al. An Automatic Magnetic Inspection Method Using Magnetoresistive Elements, Mat. Encl., May 1973, pp. 90-96.

Primary Examiner—Rudolph V. Rolinec
Assistant Examiner—Walter E. Snow
Attorney, Agent, or Firm—Steinberg & Blake

[57] ABSTRACT

A method is proposed by which defects in workpieces are detected magnetically, which method comprises the following steps being performed concurrently: scanning the test surface of a workpiece utilizing magneto-sensitive elements; magnetizing the workpiece perpendicularly to its test surface in the test zone; exciting magneto-sensitive elements; and measuring the tangential component of the magnetic field strength in the test zone. An apparatus for magnetically detecting defects in workpieces according to the proposed method comprises an electrical signal excitation/measuring unit and a detector. The latter has a housing which accommodates a core-type magnet rigidly fixed to it and adapted to be magnetized prependicularly to its working surface which mounts magneto-sensitive elements separated from each other and oriented in a prescribed manner. The elements connect each other and the electrical signal excitation/measuring unit as well.

2 Claims, 5 Drawing Figures

METHOD AND APPARATUS FOR DETECTING DEFECTS IN WORKPIECES USING A CORE-TYPE MAGNET WITH MAGNETO-SENSITIVE DETECTORS

FIELD OF THE INVENTION

This invention relates to test methods and apparatus, and more particularly to methods and apparatus for magnetically detecting defects in workpieces.

The invention is suitable for inspection of ferromagnetic materials and workpieces of complex configuration and any size.

DESCRIPTION OF THE PRIOR ART

At present, the development of modern industrial technology requires workpieces of ferromagnetic materials to have adequate quality and reliability. This, in turn, requires improved quality control including magnetic nondestructive methods. However, present-day magnetic methods of inspection, though highly effective, usually apply to a limited group of workpieces, namely, elongate ones which have simple configuration. On the other hand, workpieces of a small size and complex configuration are generally inspected using a magnetic powder method which offers a low efficiency.

Known in the art is a magnetic inspection method (cf. U.S. Pat. No. 3,710,236, issued Jan. 9, 1973) which method comprises the following steps performed concurrently: magnetizing a workpiece; exciting magneto-sensitive elements; scanning the test surface of the workpiece; and measuring the gradient of the magnetic field strength in the test zone with the help of the elements. According to this method, the workpiece is magnetized in the test zone parallel to the test surface and the gradient of that component of the strength of the magnetic field formed by a defect is measured which is perpendicular to the test surface of the workpiece.

When a workpiece is magnetized parallel to the test surface, some defects such as cracks, spills, etc., extending at an angle less than $\pi/4$ to the direction of the magnetizing field, form a magnetic field which cannot ensure the detection of the defects.

Moreover, the described method results in a zone being magnetized whose size is too great as compared with the size of the test workpiece. As a result, at the edges of the latter there results an uneven magnetic field whose strength considerably exceeds that of the magnetic field formed by a defect. The defects in a wide zone surrounding the edges of the workpiece cannot therefore be detected and workpieces of a small size and complex configuration are difficult to inspect.

There is also another method of magnetic inspection of workpieces (cf. Nondestructive Testing Reference Book, Part 2, pp. 86-93, ed. by McMaster, "Energiya" Publishers, Moscow-Leningrad, 1965) in which the following steps are performed concurrently: magnetizing a workpiece perpendicularly to the test surface; exciting magneto-sensitive elements; and measuring the gradient of the tangential component of the magnetic field strength in the test zone by means of the elements. According to this method, the magnetic field being measured is a residual magnetic field of the magnetized workpiece and is measured after the workpiece has been magnetized. According to this method the quality characteristics of the workpiece can be controlled only at separate points on its surface, and cannot therefore be controlled as a whole. Moreover, the residual magnetic field cannot detect of discontinuities in workpieces of magnetically soft materials.

The known apparatus for performing the above-described method comprises an electrical signal excitation/measuring unit and a detector having a housing which houses at least two magneto-sensitive elements electrically coupled to the electrical signal excitation/measuring unit and a core-type magnet magnetized perpendicularly to the working surface, that faces the elements. In this apparatus, the core-type magnet is positioned in movable relation to the magneto-sensitive elements and to the detector housing and is moved along the direction of magnetization.

Since a workpiece is magnetized in the use of this apparatus with the core-type magnet located between the magneto-sensitive elements, the distance between the latter cannot be less than the diameter of the core-type magnet, which therefore precludes the detection of defects with magnetic fields of a high degree of localization. Moreover, the apparatus measures the strength only at the magnetic field of a local portion of the test workpiece and the entire surface of the same cannot therefore be scanned so as to inspect its quality in a continuous manner.

SUMMARY OF THE INVENTION

An object of the invention is to provide a method for magnetically detecting defects in workpieces, which method ensures continuous inspection of quality characteristics of workpieces being tested.

Another object of the invention is to provide an apparatus for magnetically detecting defects in workpieces, which apparatus performs the proposed method and ensures continuous inspection of quality characteristics of workpieces of complex configuration and of any size.

According to the invention there is provided a method for magnetically detecting defects in workpieces, which method comprises magnetizing a workpiece perpendicularly to its test surface in the test zone, exciting magnetosensitive elements and simultaneously measuring the tangential component of the magnetic field strength in the test zone by the magneto-sensitive elements according to the method, the test surface of the workpiece is scanned utilizing the magneto-sensitive elements, the scanning of the test surface as well as the magnetization of the workpiece being accomplished during the time that the magneto-sensitive elements are excited and measure the tangential component of the magnetic field strength in the test zone.

Advantageously, the apparatus for magnetically detecting defects in workpieces comprises an electrical signal excitation/measuring unit, a detector having a housing which houses at least two magnetically sensitive elements electrically coupled to each other and to the electrical signal excitation/measuring unit, and a core-type magnet magnetized perpendicularly to its working surface which faces the magneto-sensitive elements. According to the invention, the core-type magnet is fixed immovably with respect to the housing of the detector and the magneto-sensitive elements are mounted on the working surface of the core-type magnet and are oriented so that a maximum sensitivity axis of each of the elements is perpendicular to the direction of the total magnetic field formed by the magnetic field of the core-type magnet and the magnetic field of the test workpiece and the distance between the centers of the magneto-sensitive elements is determined by the following formula:

$$A = 2\sqrt{\frac{-B + \sqrt{B^2 + 12C}}{6}}$$

where $A$ is the distance between the centers of the elements;
$B = y^2 - 2b^2 + (y+h)^2$;
$C = (b^2 + y^2)[b^2 + (y+h)^2]$;
$y$ is the distance from the centers of the elements to the test surface of the workpiece;
$b$ is the half-width of minimal defects to be detected;
$h$ is the depth of minimal defects to be detected.

The present invention makes it possible to control the characteristics of a local zone of a workpiece in the magnetic field applied thereto, which allows for continuous inspection of the surfaces of workpieces of complex configuration and any size.

With the invention, provision is made for equal magnitudes of the magnetic field strengths of extended defects irrespective of their orientation on the workpiece surface, which allows for the detection of all types of the defects available.

DESCRIPTION OF THE DRAWINGS

Other features and advantages of the invention will appear from the following description of a preferred embodiment thereof in conjunction with the accompanying in which.

DESCRIPTION OF THE INVENTION

The proposed method for magnetically detecting defects in workpieces, which method comprises concurrently scanning the test surface of a workpiece, magnetizing the latter perpendicularly to the test surface in the test zone, exciting magnetosensitive elements and measuring the gradient of the tangential component of the magnetic field strength in the test zone by means of the magneto-sensitive elements, provides for inspection of a number of quality characteristics of workpieces. Such characteristics include the thickness of non-magnetic coatings on a ferromagnetic base; mechanical and magnetic properties of workpieces; and the presence of discontinuities.

Given below is a description of the apparatus to realize the proposed method, said apparatus being operated to detect discontinuities in ferromagnetic workpieces with the help of magneto-sensitive elements incorporated in a ferromagnetic-type detecting probe.

Figure 1:
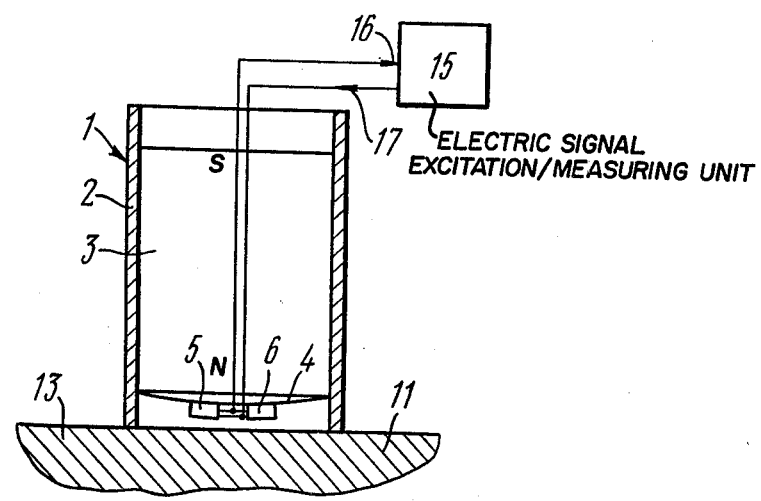
FIG. 1 is a block diagram of an apparatus for magnetically detecting defects in workpieces, according to the invention.
Figure 2:
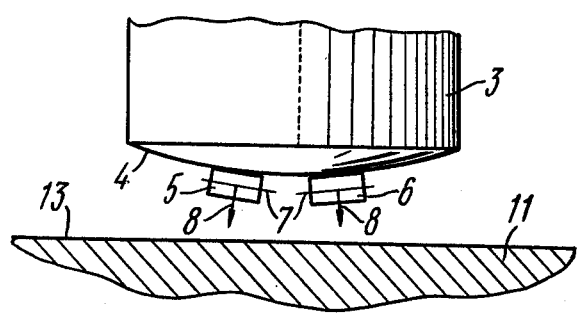
FIG. 2 shows the location of two magneto-sensitive elements on the working surface of a core-type magnet, according to the invention.
Figure 3:
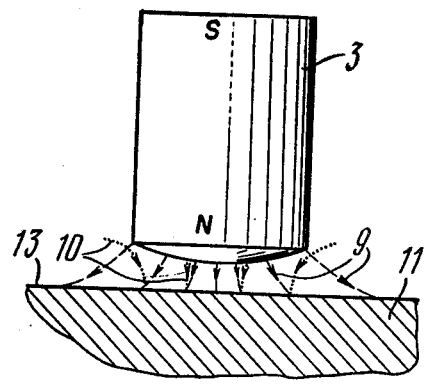
FIG. 3 shows the distribution of magnetic fields in a zone between the core-type magnet and a test workpiece, according to the invention.
Figure 4:
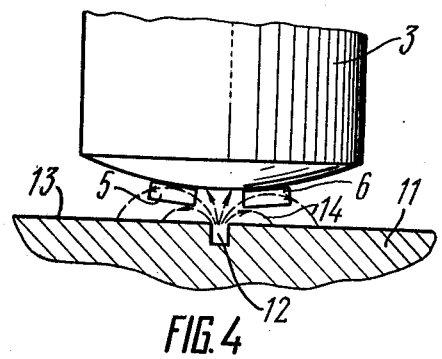
FIG. 4 shows the distribution of the magnetic field formed by a defect in the test workpiece, according to the invention.

The apparatus of the invention comprises a detector 1 (FIG. 1) having a housing 2 in which a core-type magnet 3 is fixed rigidly and which is adapted to be magnetized perpendicularly to its working surface 4. The latter mounts immovable magneto-sensitive elements 5,6 are fixedly mounted to the working surface 4 and are so oriented that a maximum sensitivity axis 7 (FIG. 2) of each of the elements 5,6 is perpendicular to a direction 8 of the total magnetic field comprised of a magnetic field 9 (FIG. 3) of the core-type magnetic 3 and a magnetic field 10 of a workpiece 11 (FIGS. 1, 2, 3). The distance between the centers of the elements 5, 6 is determined by $$A = 2\sqrt{\frac{-B + \sqrt{B^2 + 12C}}{6}} \tag{1}$$

where $A$ is the distance between the centers of the elements (5, 6);
$B = y^2 - 2b^2 + (y+h)^2$;
$C = (b^2 + y^2)[b^2 + (y+h)^2]$;
$y$ is the distance from the centers of the magneto-sensitive elements (5, 6) to a test surface 13 of the workpiece 11;
$b$ and $h$ are the half-width and the depth, respectively, of a minimal defect 12 (FIG. 4) to be detected on the test surface 13 (FIGS. 1, 2, 3, 4) of the workpiece 11 with the help of a magnetic field 14 (FIG. 4) of the defect 12.

The elements 5, 6 (FIG. 1) are coupled to each other, whereas an electric signal excitation/measuring unit 15 has its input 16 and its output 17 coupled to these elements.

Figure 5:
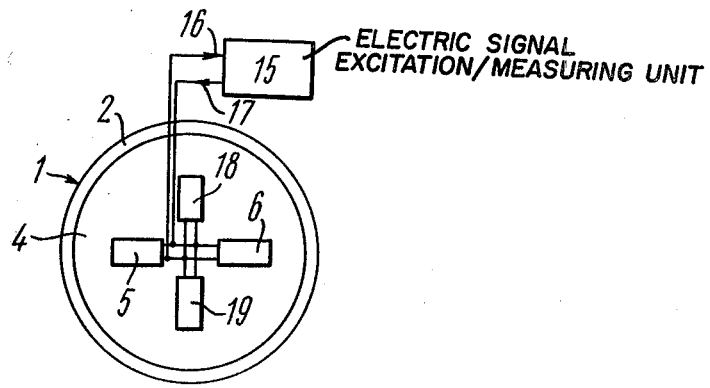
FIG. 5 show the location of four magneto-sensitive elements on the working surface of the core-type magnet, according to the invention.

According to another embodiment of the detector 1, the working surface 4 of the core-type magnet 3 has additional magneto-sensitive elements 18, 19 (FIG. 5) mounted thereon which are analogous to the elements 5, 6 (FIG. 2.). The elements 5,6 and 18,19 are arranged in two respective pairs at right angles to each other. The elements 18, 19 are connected to each other and to the unit 15 in a manner similar to that described for the elements 5, 6.

The proposed apparatus operates as follows. The detector 1 (FIG. 1) is placed on the test surface 13 of the workpiece 11. That portion of the workpiece 11 which engages the working surface of the detector 1 is magnetized by the magnetic field of the core-type magnetic 3 perpendicularly to the test surface 13 of the workpiece 11. In the zone extending between the core-type magnet 3 and the test surface 13 of the workpiece 11 there results a total magnetic field comprised of the magnetic field 9 (FIG. 3) formed by the core-type magnet 3 and the magnetic field 10 of the magnetized workpiece 11.

After the detector 1 (FIG. 1) is placed on the test surface 13 of the workpiece 11, the magneto-sensitive elements 5, 6 are excited using a signal from the output 17 of the unit 15, the test surface 13 is scanned and a signal delivered from the elements 5, 6 to the input 16 of the unit 15 is measured. The elements 5,6 (FIG. 2) are so oriented that the maximum sensitivity axis 7 of each of them is perpendicular to the direction 8 of the total magnetic field. This provides for a condition in which the elements 5,6 produce a signal whose magnitude equals to a zero background when a flawless portion appears on the test surface 13 (FIG. 1), that signal being applied to the input 16 of the unit 15.

When the defect 12 (FIG. 4) appears in the magnetized zone of the workpiece 11, namely, in the test zone, the resulting magnetic field 14 is established. The tangential component of the strength of the magnetic field 14 acts on the elements 5,6 as much as possible, since the maximum sensitivity axis 7 (FIG. 2) of each of the elements 5, 6 passes through the test surface 13 at an angle less than $\pi/4$. The value of that tangential component is determined by $$H_T = \ln \frac{\left[(\frac{A}{2}+y)^2 + y^2\right]\left[(\frac{A}{2}-b_1)^2 + (y+h_1)^2\right]}{\left[(\frac{A}{2}-y)^2 + y^2\right]\left[(\frac{A}{2}+b_1)^2 + (y+h_1)^2\right]} \quad (2)$$

where

H is the value of the tangential component of the strength of the magnetic field 14 (FIG. 4) formed by the defect 12, expressed in terms of relative units;

$b_1$ and $h_1$ are the half-width and the depth of the defect 12, respectively.

When influenced by the magnetic field 14, the elements 5, 6 produce a useful signal exceeding a zero background, this signal being applied to the input 16 (FIG. 1) of the unit 15. The unit 15 registers any defect 12 (FIG. 4) whose dimensions exceed those of a minimal defect and which is sensed by the detector 1 (FIG. 1). This is due to the fact that the distance between the elements 5, 6 is selected according to (1) derived from (2) and that an optimum criterion of detection of minimal defects is satisfied.

If the direction of the magnetizing field is perpendicular to the test surface 13 of the workpiece 11, then the strength of the magnetic field 14 (FIG. 4) of the defect 12 is not dependent upon the orientation of that defect with respect to the test surface 13, which enables defects 12 extending through any desirable direction to be detected. It is common practice to turn the detector 1 (FIG. 1) in this case about its longitudinal axis and to scan simultaneously the surface 13. Also, it is preferable to utilize the detector 1 comprised of four magneto-sensitive elements 5, 6, 18, 19 (FIG. 5) and operated in a manner analogous to that described for the detector 1 (FIG. 2) having two magneto-sensitive elements 5, 6.

The present invention tends to cut down inspection expenditures in the case of workpieces of complex configuration due to a higher speed of the operational steps of the method and due to lower power requirements.

Moreover, reclamation expenditures are reduced due to the fact that a broader list of workpieces tested is available along with a decrease in harmful edge effects and an increase in the quality of detecting variously oriented superficial defects.

The invention also yields and economic effect for both post-process and process inspection since expenditures for materials and labor, in terms of the unit of product, are reduced and test results influence production processes.

The invention provides a detector of a simpler design, which results in a saving of materials used for its manufacture.

What is claimed is:

1. A method for detecting defects in workpieces utilizing a detector including a core-type magnet substantially perpendicular to the workpiece and has been added, having a working surface, at least two magneto-sensitive elements mounted on the working surface of the magnet with the axis of maximum sensitivity of each magneto-sensitive element being oriented perpendicular to the direction of the total magnetic field formed by said core-type magnet and the magnetic field formed by said workpiece and an electrical signal excitation/-measuring unit having an input and an output coupled to the magneto-sensitive elements, comprising the following steps being performed concurrently:

scanning a test surface of a workpiece by moving the detector over the test surface with the magneto-sensitive elements in spaced, opposed relationship thereto;

magnetizing the workpiece perpendicularly to said test surface in a test zone under the action of the magnetic field of the core-type magnet;

exciting the magneto-sensitive elements by actuation of the excitation/measuring unit; and measuring the gradient of the tangential component of the magnetic field comprised by the magnetic field of the core-type magnet and the magnetic field of the magnetized workpiece in the test zone.

2. An apparatus for detecting defects in workpieces comprising:

a detector mounted within a housing and adapted to be passed over a workpiece surface which is to be tested for defects;

a core-type magnet of said detector fixed within said housing, one surface of which comprises a working surface, said core-type magnet being magnetized perpendicularly to said working surface;

at least two magneto-sensitive elements of said detector mounted on said working surface of said core-type magnet;

each of said magneto-sensitive elements having a maximum sensitivity axis and a center;

said maximum sensitivity axis of each said magneto-sensitive element being oriented perpendicularly to the direction of the total magnetic field comprised of the magnetic field formed by said core-type magnet and the magnetic field formed by said workpiece;

the distance between said centers of said magnetosensitive elements being:

$$A = 2\sqrt{\frac{-B + \sqrt{B^2 + 12C}}{6}}$$

where

A is the distance between the centers of said magnetosensitive elements;

$B = y^2 - 2B^2 + (y+h)^2$;

$C = (b^2 + y^2)[b^2 + (y+h)^2]$ y is the distance from said centers of said magnetosensitive elements to said test surface of said workpiece;

b and h are the half-width and the depth, respectively, of said defects to be detected; and an electrical signal excitation/measuring unit having an input and an output coupled to said magneto-sensitive elements.

* * * * *